United States Patent
Park et al.

(10) Patent No.: US 11,031,629 B2
(45) Date of Patent: Jun. 8, 2021

(54) ELECTROLYTE OF RECHARGEABLE LITHIUM BATTERY AND RECHARGEABLE LITHIUM BATTERY INCLUDING SAME

(71) Applicant: Samsung SDI Co., Ltd., Yongin-si (KR)

(72) Inventors: Hyejin Park, Yongin-si (KR); Jungjin Moon, Yongin-si (KR); Myungheui Woo, Yongin-si (KR); Harim Lee, Yongin-si (KR); Jin-Hyeok Lim, Yongin-si (KR); Seonghun Jeong, Yongin-si (KR); Wonseok Cho, Yongin-si (KR); Hyunbong Choi, Yongin-si (KR)

(73) Assignee: Samsung SDI Co., Ltd., Yongin-si (KR)

( * ) Notice: Subject to any disclaimer, the term of this patent is extended or adjusted under 35 U.S.C. 154(b) by 226 days.

(21) Appl. No.: 16/373,374

(22) Filed: Apr. 2, 2019

(65) Prior Publication Data
US 2019/0312308 A1    Oct. 10, 2019

(30) Foreign Application Priority Data

Apr. 5, 2018 (KR) .......................... 10-2018-0039876
Sep. 7, 2018 (KR) .......................... 10-2018-0107029

(51) Int. Cl.
*H01M 10/0567*    (2010.01)
*H01M 10/0568*    (2010.01)
(Continued)

(52) U.S. Cl.
CPC ... *H01M 10/0567* (2013.01); *H01M 10/0568* (2013.01); *H01M 10/0569* (2013.01);
(Continued)

(58) Field of Classification Search
None
See application file for complete search history.

(56) References Cited

U.S. PATENT DOCUMENTS

| 6,927,001 B1 | 8/2005 | Hamamoto et al. |
| 2014/0038062 A1* | 2/2014 | Kawakami ........ H01M 10/0568 429/338 |

(Continued)

FOREIGN PATENT DOCUMENTS

| JP | 10-189041 A | 7/1998 |
| JP | 3823683 B2 | 9/2006 |

(Continued)

OTHER PUBLICATIONS

Notice of Allowance issued in corresponding Korean Patent Application No. 10-2018-0107029 dated Mar. 30, 2021, 6 pgs.

*Primary Examiner* — Wyatt P McConnell
(74) *Attorney, Agent, or Firm* — Lewis Roca Rothgerber Christie LLP

(57) ABSTRACT

Aspects of embodiments of the present disclosure provide an electrolyte for a rechargeable lithium battery, and a rechargeable lithium battery including the same. The electrolyte includes a non-aqueous organic solvent, a lithium salt, and additive represented by Chemical Formula 1:

Chemical Formula 1

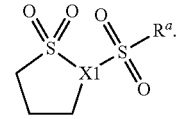

In Chemical Formula 1, X1 is CH or a nitrogen atom (N), and $R^a$ is a substituted or unsubstituted alkyl group. The (Continued)

additive may decompose under reducing voltages on the surface of the negative electrode to thereby form a polysulfonate-based passivation film to suppress or reduce gas generation and battery swelling.

13 Claims, 2 Drawing Sheets

(51) Int. Cl.
*H01M 10/0569* (2010.01)
*C07D 275/02* (2006.01)
*H01M 10/0525* (2010.01)

(52) U.S. Cl.
CPC ....... *C07D 275/02* (2013.01); *H01M 10/0525* (2013.01); *H01M 2300/0025* (2013.01)

(56) References Cited

U.S. PATENT DOCUMENTS

| 2014/0134501 A1 | 5/2014 | Li et al. |
| 2017/0069935 A1 | 3/2017 | Choi et al. |

FOREIGN PATENT DOCUMENTS

| JP | 2007-172990 A | 7/2007 |
| KR | 10-2015-0114460 A | 10/2015 |
| KR | 10-2017-0028677 A | 3/2017 |

* cited by examiner

ELECTROLYTE OF RECHARGEABLE LITHIUM BATTERY AND RECHARGEABLE LITHIUM BATTERY INCLUDING SAME

CROSS-REFERENCE TO RELATED APPLICATION

This application claims priority to and the benefit of Korean Patent Application No. 10-2018-0039876, filed in the Korean Intellectual Property Office on Apr. 5, 2018, and Korean Patent Application No. 10-2018-0107029, filed in the Korean Intellectual Property Office on Sep. 7, 2018, the entire content of each of which is incorporated herein by reference.

BACKGROUND

1. Field

One or more aspects of example embodiments of the present disclosure are related to an electrolyte for a rechargeable lithium battery and a rechargeable lithium battery including the same.

2. Description of the Related Art

Rechargeable lithium batteries are attractive power sources for electronic devices due, in part, to their high discharge voltages and/or high energy densities.

Lithium-transition metal oxides having a structure capable of intercalating and deintercalating lithium ions (such as $LiCoO_2$, $LiMn_2O_4$, $LiNi_{1-x}Co_xO_2$ ($0<x<1$), and the like) have been used as positive active materials in rechargeable lithium batteries.

Various suitable carbon-based materials capable of intercalating and deintercalating lithium ions (such as artificial graphite, natural graphite, and/or hard carbon) have been used as negative active materials in rechargeable lithium batteries.

Various suitable lithium salts dissolved in a suitable organic solvent have been used as electrolytes in rechargeable lithium batteries.

When rechargeable lithium batteries are stored at a high temperature, there is a problem that the thicknesses of the batteries may significantly expand due to generation of gas (e.g., produced by electrolyte decomposition).

SUMMARY

One or more aspects of example embodiments of the present disclosure are directed toward an electrolyte for a rechargeable lithium battery, the electrolyte being capable of suppressing or reducing gas generation during high temperature storage (e.g., storage at temperatures above about 25° C.), thereby suppressing or reducing cell thickness expansion.

One or more aspects of example embodiments of the present disclosure are directed toward a rechargeable lithium battery including the electrolyte.

One or more example embodiments of the present disclosure provide an electrolyte for a rechargeable lithium battery that includes a non-aqueous organic solvent, a lithium salt, and an additive represented by Chemical Formula 1:

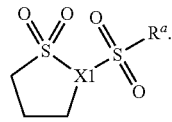

Chemical Formula 1

In Chemical Formula 1, X1 may be CH or a nitrogen atom (N), and $R^a$ may be a substituted or unsubstituted alkyl group. In some embodiments, the substituted alkyl group may be a fluorine-substituted alkyl group.

An amount of the additive may be about 0.1 wt % to about 3 wt % based on a total weight of the electrolyte. In some embodiments, an amount of the additive may be about 1 wt % to about 2 wt % based on the total weight of the electrolyte.

In some embodiments, the electrolyte may further include a second additive selected from fluoroethylene carbonate, vinylene carbonate, succinonitrile, hexane tricyanide, $LiBF_4$, and combinations thereof. An amount of the second additive may be about 5 wt % to about 20 wt % based on the total weight of the electrolyte.

One or more example embodiments of the present disclosure provide a rechargeable lithium battery including: a negative electrode including a negative active material; a positive electrode including a positive active material; and the electrolyte.

Additional embodiments are described in the following detailed description.

The electrolyte for a rechargeable lithium battery according to one or more embodiments of the present disclosure may improve the storage characteristics of the battery at high temperature, for example, high temperature swelling properties.

DETAILED DESCRIPTION

Figure 1:
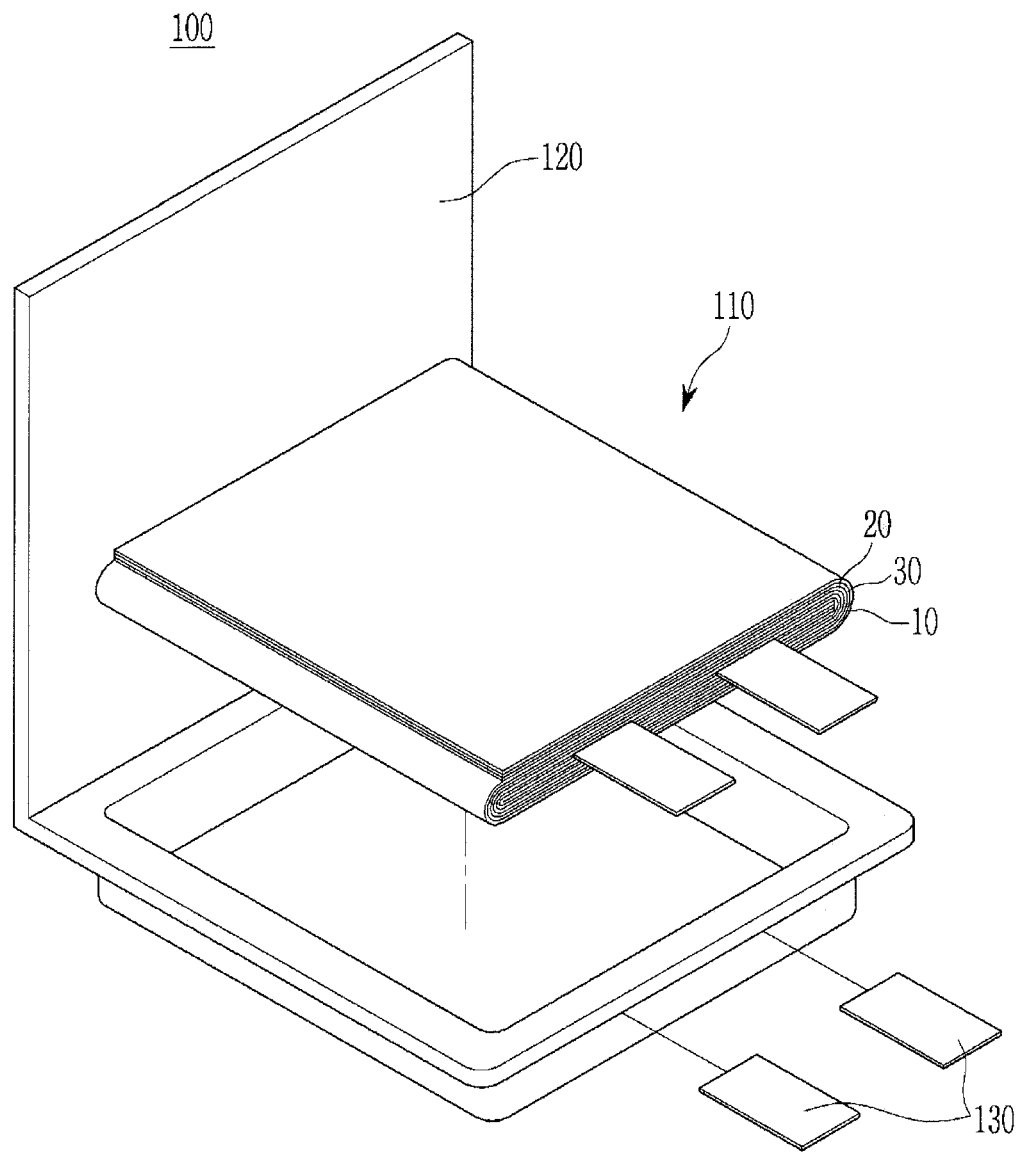
FIG. 1 is a schematic view of a rechargeable lithium battery according to an embodiment of the present disclosure.

Hereinafter, various embodiments of the present disclosure will be described in more detail. References will be made to example embodiments, examples of which are illustrated in the accompanying drawings, wherein like reference numerals refer to like elements throughout and duplicative descriptions thereof may not be provided. It will be understood that these embodiments are provided as examples, and that the present disclosure is not limited thereto. In this regard, the present example embodiments may have different forms and should not be construed as being limited to the descriptions set forth herein. Accordingly, the example embodiments are merely described below, by referring to the drawings, to explain one or more aspects of the present description.

Expressions such as "at least one of", "one of", and "selected from", when preceding a list of elements, modify the entire list of elements and do not modify the individual elements of the list. Further, the use of "may" when describing embodiments of the present disclosure refers to "one or more embodiments of the present disclosure."

In the drawings, the thicknesses of layers, films, panels, regions, etc., may be exaggerated for clarity. It will be understood that when an element such as a layer, film, region, or substrate is referred to as being "on" another element, it can be directly on the other element or intervening element(s) may also be present. In contrast, when an element is referred to as being "directly on" another element, no intervening elements are present.

One or more embodiments of the present disclosure provide an electrolyte for a rechargeable lithium battery including: a non-aqueous organic solvent, a lithium salt, and additive represented by Chemical Formula 1:

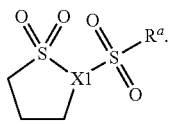

Chemical Formula 1

In Chemical Formula 1, X1 may be CH or a nitrogen atom (N), in some embodiments, X1 may be N. In Chemical Formula 1, $R^a$ may be a substituted or unsubstituted alkyl group. In some embodiments, the alkyl group may be a $C_1$ to $C_{20}$ alkyl group, and in some embodiments, the alkyl group may be a linear or branched alkyl group. Non-limiting examples of the linear alkyl group include a substituted or unsubstituted methyl group, a substituted or unsubstituted ethyl group, a substituted or unsubstituted propyl group, a substituted or unsubstituted butyl group, a substituted or unsubstituted pentyl group, and a substituted or unsubstituted hexyl group, a substituted or unsubstituted heptyl group, a substituted or unsubstituted octyl group, a substituted or unsubstituted nonyl group, a substituted or unsubstituted decyl group, a substituted or unsubstituted dodecyl group, etc. Non-limiting examples of the branched alkyl group include a substituted or unsubstituted isopropyl group, a substituted or unsubstituted sec-butyl group, a substituted or unsubstituted isobutyl group, a substituted or unsubstituted neopentyl group, a substituted or unsubstituted isopentyl group, etc. In some embodiments, the substituted alkyl group may be a fluorine-substituted alkyl group. The substituted alkyl group may be substituted in the middle of the alkyl group, or at a terminal end of the alkyl group. For example, the substituted alkyl group may be an alkyl group in which at least one hydrogen is replaced by a fluorine atom, for example, $-(CF_2)_n-CF_3$ (wherein n is an integer ranging from 0 to 20).

In some embodiments, non-limiting examples of Chemical Formula 1 include Chemical Formula 1a and Chemical Formula 1b:

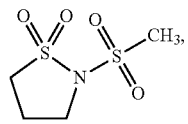

Chemicial Formula 1a

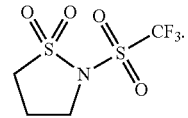

Chemical Formula 1b

When a battery using the electrolyte including the additive according to embodiments of the present disclosure is charged and discharged, the additive may decompose to form a stable passivation film (e.g., a solid electrolyte layer, solid electrolyte interphase (SEI) film, etc.) on a surface of the negative electrode. The stable passivation film may have improved lithium ion transporting properties and may be stable at high temperature storage (e.g., may improve the stability of the electrolyte and/or solvent at temperatures above about 25° C.), thereby suppressing or reducing generation of gas, resulting in decreased battery swelling.

As shown in Chemical Formula 1, when the additive according to one or more embodiments of the present disclosure includes a sulfur atom (S) in its 5-membered ring and a $-SO_2R^a$ group bound to the 5-membered ring, the additive may be reduction-decomposed on the surface of the negative electrode to thereby form a polysulfonate-based passivation film having excellent thermal stability, which may improve the storage characteristics (stability) of the battery at high temperatures. When the 5-membered ring includes N along with S (i.e., X1 is a nitrogen atom (N)) and the $-SO_2R^a$ group is bound to the N in the 5-membered ring, such characteristics may be further maximized or increased.

When the 5-membered ring does not include a S atom, or an alkyl group is bound (e.g., directly bound) to the 5-membered ring even if S is included (e.g., without an intervening $SO_2$ group), a passivation film may be excessively formed, resulting in increased initial thickness and battery resistance.

For example, propane sultone has been used to improve swelling properties during high temperature storage of batteries in the related art, and while the swelling properties were improved, batteries including propane sultone were found to have increased battery resistance, resulting in deteriorated capacity retention and capacity recovery rates. However, the additive of Chemical Formula 1 according to one or more embodiments of the present disclosure does not increase resistance while forming a stable passivation film at high temperatures, and may thereby effectively improve swelling properties, the capacity retention, and/or the recovery rate of batteries under high-temperature storage conditions.

An amount of the additive may be about 0.1 wt % to about 3 wt % based on a total weight of the electrolyte, and in some embodiments, may be about 1 wt % to about 2 wt % based on the total weight of the electrolyte. When the amount of the additive is within the above ranges, generation of gas (e.g., due to decomposition of the electrolyte) may be limited or decreased during storage of the battery, and storage characteristics at high temperatures may be further improved. When the amount of the additive is less than about 0.1 wt %, the passivation film may not be sufficiently formed on the surface of the negative electrode, and the effect of improving the high-temperature properties may be insignificant. When the amount of the additive is greater than about 3 wt %, the electrolyte may severely decompose with an increase in generated gas, such that the initial thickness and battery resistance may be increased.

In some embodiments, the electrolyte may further include a second additive selected from fluoroethylene carbonate, vinylene carbonate, succinonitrile, hexane tricyanide, $LiBF_4$, and combinations thereof, in addition to the above additive (which may alternatively be referred to as a first additive). When the second additive is further included, it may be possible to form a more rigid (e.g., stable) passivation film on the surface of the negative electrode, to stabilize the interface between the positive electrode and the electrolyte, and further prevent or reduce additional electrolyte decomposition. When the second additive is further included, an amount of the second additive may be about 5 wt % to about 20 wt % based on the total weight of the electrolyte. When the second additive is included within this range, the effects of using the second additive may be suitably obtained. When the second additive is used in an excessive amount (e.g., an amount exceeding the above ranges), the resistance of the battery may be excessively increased, causing deterioration of the battery over repeated charging/discharging cycles. When the second additive includes a mixture of fluoroethylene carbonate, vinylene carbonate, succinonitrile, hexane tricyanide, or $LiBF_4$, a mixing ratio may be adjusted, without limitation, to have any suitable ratio.

The non-aqueous organic solvent serves as a medium for transmitting ions (e.g., $Li^+$) taking part in the electrochemical reactions of a battery.

The non-aqueous organic solvent may include a carbonate-based, ester-based, ether-based, ketone-based, alcohol-based, and/or aprotic solvent.

Non-limiting examples of the carbonate based solvent include dimethyl carbonate (DMC), diethyl carbonate (DEC), dipropyl carbonate (DPC), methylpropyl carbonate (MPC), ethylpropyl carbonate (EPC), methylethyl carbonate (MEC), ethylene carbonate (EC), propylene carbonate (PC), butylene carbonate (BC), and the like. Non-limiting examples of the ester-based solvent include methyl acetate, ethyl acetate, n-propyl acetate, dimethylacetate, methylpropionate, ethylpropionate, propylpropionate, γ-butyrolactone, decanolide, valerolactone, mevalonolactone, caprolactone, and the like.

Non-limiting examples of the ether-based solvent include dibutyl ether, tetraglyme, diglyme, dimethoxyethane, 2-methyltetrahydrofuran, tetrahydrofuran, and the like. Non-limiting examples of the ketone-based solvent include cyclohexanone and the like.

Non-limiting examples of the alcohol-based solvent include ethanol, isopropyl alcohol, and the like. Non-limiting examples of the aprotic solvent include nitriles (such as T-CN and the like, wherein T is a hydrocarbon group having a $C_2$ to $C_{20}$ linear, branched, or cyclic structure, and may include a double bond, an aromatic ring, and/or an ether bond), dioxolanes (such as 1,3-dioxolane and the like), sulfolanes, and the like.

The non-aqueous organic solvent may be used alone or in a mixture. When the organic solvent is used in a mixture, the mixture ratio may be controlled or selected in accordance with a desirable or suitable battery performance.

The carbonate-based solvent may be prepared by mixing a cyclic carbonate and a linear carbonate. When the cyclic carbonate and linear carbonate are mixed together in a volume ratio of about 1:1 to about 1:9, the performance of a battery including the electrolyte solution may be improved.

In some embodiments, the non-aqueous organic solvent may further include an aromatic hydrocarbon-based organic solvent in addition to the carbonate-based solvent. The carbonate-based solvent and the aromatic hydrocarbon-based organic solvent may be mixed in a volume ratio of about 1:1 to about 30:1.

The aromatic hydrocarbon-based organic solvent may be an aromatic hydrocarbon-based compound represented by Chemical Formula 2:

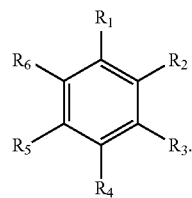

Chemical Formula 2

In Chemical Formula 2, $R_1$ to $R_6$ may be the same or different, and may be selected from hydrogen, a halogen, a $C_1$ to $C_{10}$ alkyl group, a haloalkyl group, and combinations thereof.

Non-limiting examples of the aromatic hydrocarbon-based organic solvent include benzene, fluorobenzene, 1,2-difluorobenzene, 1,3-difluorobenzene, 1,4-difluorobenzene, 1,2,3-trifluorobenzene, 1,2,4-trifluorobenzene, chlorobenzene, 1,2-dichlorobenzene, 1,3-dichlorobenzene, 1,4-dichlorobenzene, 1,2,3-trichlorobenzene, 1,2,4-trichlorobenzene, iodobenzene, 1,2-diiodobenzene, 1,3-diiodobenzene, 1,4-diiodobenzene, 1,2,3-triiodobenzene, 1,2,4-triiodobenzene, toluene, fluorotoluene, 2,3-difluorotoluene, 2,4-difluorotoluene, 2,5-difluorotoluene, 2,3,4-trifluorotoluene, 2,3,5-trifluorotoluene, chlorotoluene, 2,3-dichlorotoluene, 2,4-dichlorotoluene, 2,5-dichlorotoluene, 2,3,4-trichlorotoluene, 2,3,5-trichlorotoluene, iodotoluene, 2,3-diiodotoluene, 2,4-diiodotoluene, 2,5-diiodotoluene, 2,3,4-triiodotoluene, 2,3,5-triiodotoluene, xylene, and combinations thereof.

The electrolyte of a rechargeable lithium battery may further include an ethylene carbonate-based compound represented by Chemical Formula 3 in order to improve battery cycle life:

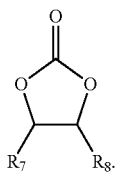

Chemical Formula 3

In Chemical Formula 3, $R_7$ and $R_8$ may each independently be selected from hydrogen, a halogen atom (such as F, Cl, Br, and/or I), a cyano group (CN), a nitro group ($NO_2$), and a fluorinated $C_1$ to $C_5$ alkyl group, provided that at least one of $R_7$ and $R_8$ is selected from a halogen atom, a cyano group (CN), a nitro group ($NO_2$), and a fluorinated $C_1$ to $C_5$ alkyl group, and $R_7$ and $R_8$ are not simultaneously (e.g., both or concurrently) hydrogen.

Non-limiting examples of the ethylene carbonate-based compound include difluoroethylene carbonate, chloroethylene carbonate, dichloroethylene carbonate, bromoethylene carbonate, dibromoethylene carbonate, nitroethylene carbonate, cyanoethylene carbonate, fluoroethylene carbonate, and the like. The amount of the additive for improving cycle life may be within a suitable range.

The lithium salt dissolved in an organic solvent supplies lithium ions in a battery, enables basic operation of a rechargeable lithium battery, and improves lithium ion transport between the positive and negative electrodes. Non-limiting examples of the lithium salt include at least one supporting salt selected from $LiPF_6$, $LiSbF_6$, $LiAsF_6$, $LiN(SO_2C_2F_5)_2$, $Li(CF_3SO_2)_2N$, $LiN(SO_3C_2F_5)_2$, $LiC_4F_9SO_3$, $LiClO_4$, $LiAlO_2$, $LiAlCl_4$, $LiN(C_xF_{2x+1}SO_2)(C_yF_{2y+1}SO_2)$ (wherein x and y are natural numbers, for example, an integer ranging from 1 to 20), LiCl, LiI, and $LiB(C_2O_4)_2$ (lithium bis(oxalato) borate; LiBOB). The lithium salt may be used in a concentration of about 0.1 M to about 2.0 M. When the lithium salt is included in the above concentration range, the electrolyte may have excellent performance and/or lithium ion mobility due to optimal or suitable electrolyte conductivity and/or viscosity.

One or more embodiments of the present disclosure provide a rechargeable lithium battery including the electrolyte, a positive electrode, and a negative electrode.

The positive electrode may include a current collector and a positive active material layer on the current collector, the positive active material layer including a positive active material.

In the positive active material layer, the positive active material may include a compound (lithium intercalation compound) capable of intercalating and deintercalating lithium. At least one composite oxide including lithium and a metal, selected from cobalt, manganese, nickel, and combinations thereof, may be used. Non-limiting examples thereof include a compound represented by one of the following chemical formulae: $Li_aA_{1-b}X_bD_2$ (0.90≤a≤1.8, 0≤b≤0.5); $Li_aA_{1-b}X_bO_{2-c}D_c$ (0.90≤a≤1.8, 0≤b≤0.5, 0≤c≤0.05); $Li_aE_{1-b}X_bO_{2-c}D_c$ (0.90≤a≤1.8, 0≤b≤0.5, 0≤c≤0.05); $Li_aE_{2-b}X_bO_{4-c}D_c$ (0.90≤a≤1.8, 0≤b≤0.5, 0≤c≤0.05); $Li_aNi_{1-b-c}Co_bX_cD_\alpha$ (0.90≤a≤1.8, 0≤b≤0.5, 0≤c≤0.5, 0<α≤2); $Li_aNi_{1-b-c}Co_bX_cO_{2-\alpha}T_\alpha$ (0.90≤a≤1.8, 0≤b≤0.5, 0≤c≤0.05, 0<α<2); $Li_aNi_{1-b-c}Co_bX_cO_{2-\alpha}T_2$ (0.90≤a≤1.8, 0≤b≤0.5, 0≤c≤0.05, 0<α<2); $Li_aNi_{1-b-c}Mn_bX_cD_\alpha$ (0.90≤a≤1.8, 0≤b≤0.5, 0≤c≤0.05, 0<α≤2); $Li_aNi_{1-b-c}Mn_bX_cO_{2-\alpha}T_\alpha$ (0.90≤a≤1.8, 0≤b≤0.5, 0≤c≤0.05, 0<α<2); $Li_aNi_{1-b-c}Mn_bX_cO_{2-\alpha}T_2$ (0.90≤a≤1.8, 0≤b≤0.5, 0≤c≤0.05, <α<2); $Li_aNi_bE_cG_dO_2$ (0.90≤a≤1.8, 0≤b≤0.9, 0≤c≤0.5, 0.001≤d≤0.1); $Li_aNi_bCo_cMn_dG_eO_2$ (0.90≤a≤1.8, 0≤b≤0.9, 0≤c≤0.5, 0≤d≤0.5, 0.001≤e≤0.1); $Li_aNiG_bO_2$ (0.90≤a≤1.8, 0.001≤b≤0.1) $Li_aCoG_bO_2$ (0.90≤a≤1.8, 0.001≤b≤0.1); $Li_aMn_{1-b}G_bO_2$ (0.90≤a≤1.8, 0.001≤b≤0.1); $Li_aMn_2G_bO_4$ (0.90≤a≤1.8, 0.001≤b≤0.1); $Li_aMn_{1-g}G_gPO_4$ (0.90≤a≤1.8, 0≤g≤0.5); $QO_2$; $QS_2$; $LiQS_2$; $V_2O_5$; $LiV_2O_5$; $LiZO_2$; $LiNiVO_4$; $Li_{(3-f)}J_2(PO_4)_3$ (0≤f≤2); $Li_{(3-f)}Fe_2(PO_4)_3$; and $Li_aFePO_4$ (0.90≤a≤1.8).

In each of the above chemical formulae, A may be selected from Ni, Co, Mn, and combinations thereof; X may be selected from Al, Ni, Co, Mn, Cr, Fe, Mg, Sr, V, a rare earth element, and combinations thereof; D may be selected from O, F, S, P, and combinations thereof; E may be selected from Co, Mn, and combinations thereof; T may be selected from F, S, P, and combinations thereof; G may be selected from Al, Cr, Mn, Fe, Mg, La, Ce, Sr, V, and combinations thereof; Q may be selected from Ti, Mo, Mn, and combinations thereof; Z may be selected from Cr, V, Fe, Sc, Y, and combinations thereof; and J may be selected from V, Cr, Mn, Co, Ni, Cu, and combinations thereof.

The lithium intercalation compound may include a coating layer on its surface (e.g., particle surfaces), and/or may be mixed with another compound having a coating layer. The coating layer may include at least one coating element compound selected from an oxide of a coating element, a hydroxide of a coating element, an oxyhydroxide of a coating element, an oxycarbonate of a coating element, and a hydroxycarbonate of a coating element. The coating layer compound may be amorphous, crystalline, or a mixture thereof. The coating element included in the coating layer may include magnesium (Mg), aluminum (Al), cobalt (Co), potassium (K), sodium (Na), calcium (Ca), silicon (Si), titanium (Ti), vanadium (V), tin (Sn), germanium (Ge), gallium (Ga), boron (B), arsenic (As), zirconium (Zr), or mixtures thereof. The coating layer may be applied using any suitable method having no adverse influence on the properties of the positive active material. For example, the coating method may include spray coating, dipping, etc.

In the positive electrode, the positive active material may be included in an amount of about 90 wt % to about 98 wt % based on a total weight of the positive active material layer.

In some embodiments, the positive active material layer may include a binder and/or a conductive material. The binder and the conductive material may each be included in an amount of about 1 wt % to about 5 wt % based on the total amount of the positive active material layer.

The binder may improve the binding properties of particles of the positive active material with one another and with the current collector. Non-limiting examples thereof include polyvinyl alcohol, carboxymethyl cellulose, hydroxypropyl cellulose, diacetyl cellulose, polyvinylchloride, carboxylated polyvinylchloride, polyvinylfluoride, an ethylene oxide-containing polymer, polyvinylpyrrolidone, polyurethane, polytetrafluoroethylene, polyvinylidene fluoride, polyethylene, polypropylene, a styrene-butadiene rubber, an acrylated styrene-butadiene rubber, an epoxy resin, nylon, and the like, but embodiments of the present disclosure are not limited thereto.

The conductive material may provide or increase electrode conductivity. Any electrically conductive material may be used as a conductive material unless it causes an unwanted chemical change (e.g., reaction). Non-limiting examples of the conductive material include a carbon-based material (such as natural graphite, artificial graphite, carbon black, acetylene black, Ketjenblack, a carbon fiber, and the like); a metal-based material (such as a metal powder and/or a metal fiber including copper, nickel, aluminum, silver, and the like); a conductive polymer (such as a polyphenylene derivative); and mixtures thereof.

The current collector may be an aluminum foil, a nickel foil, or a combination thereof, but embodiments of the present disclosure are not limited thereto.

The negative electrode may include a current collector and a negative active material layer on the current collector, the negative active material layer including a negative active material.

The negative active material may include a material capable of reversibly intercalating/deintercalating lithium ions, a lithium metal, a lithium metal alloy, a material capable of doping/dedoping lithium, and/or transition metal oxide.

The material that reversibly intercalates/deintercalates lithium ions may include a carbon material, such as any suitable carbon-based negative active material available in the art for use in a rechargeable lithium battery. Non-limiting examples of the carbon-based negative active material include crystalline carbon, amorphous carbon, and mixtures thereof. The crystalline carbon may be non-shaped natural graphite and/or artificial graphite (e.g., without a set or particular shape), or may be sheet, flake, spherical, and/or fiber shaped natural graphite and/or artificial graphite. The amorphous carbon may be a soft carbon, a hard carbon, a mesophase pitch carbonization product, fired coke, and/or the like.

The lithium metal alloy may include an alloy of lithium and a metal selected from sodium (Na), potassium (K), rubidium (Rb), cesium (Cs), francium (Fr), beryllium (Be), magnesium (Mg), calcium (Ca), strontium (Sr), silicon (Si), antimony (Sb), lead (Pb), indium (In), zinc (Zn), barium (Ba), radium (Ra), germanium (Ge), aluminum (Al), tin (Sn), and combinations thereof.

The material capable of doping/dedoping lithium may be Si, $SiO_x$ (0<x<2), a Si-Q alloy (wherein Q is an element selected from an alkali metal, an alkaline earth metal, a Group 13 element, a Group 14 element excluding Si, a Group 15 element, a Group 16 element, a transition metal, a rare earth element, and combinations thereof), a Si-carbon composite, Sn, $SnO_2$, a Sn—R alloy (wherein R is an element selected from an alkali metal, an alkaline earth metal, a Group 13 element, a Group 14 element excluding Sn, a Group 15 element, a Group 16 element, a transition metal, a rare earth element, and combinations thereof), a Sn-carbon composite, and/or the like. At least one of these materials may be mixed with $SiO_2$. The elements Q and R may be selected from Mg, Ca, Sr, Ba, Ra, scandium (Sc), yttrium (Y), titanium (Ti), zirconium (Zr), hafnium (Hf), rutherfordium (Rf), vanadium (V), niobium (Nb), tantalum (Ta), dubnium (Db), chromium (Cr), molybdenum (Mo), tungsten (W), seaborgium (Sg), technetium (Tc), rhenium (Re), bohrium (Bh), iron (Fe), lead (Pb), ruthenium (Ru), osmium (Os), hassium (Hs), rhodium (Rh), iridium (Ir), palladium (Pd), platinum (Pt), copper (Cu), silver (Ag), gold (Au), zinc (Zn), cadmium (Cd), boron (B), Al, Ga, Sn, In, Ge, phosphorus (P), As, antimony (Sb), bismuth (Bi), sulfur (S), selenium (Se), tellurium (Te), polonium (Po), and combinations thereof.

In some embodiments, the transition metal oxide may include lithium titanium oxide.

The negative active material layer may include a negative active material, a binder, and optionally a conductive material.

In the negative active material layer, the negative active material may be included in an amount of about 95 wt % to about 99 wt % based on a total weight of the negative active material layer. A content or amount of the binder may be about 1 wt % to about 5 wt % based on the total weight of the negative active material layer. When the negative active material layer includes a conductive material, the negative active material layer may include about 90 wt % to about 98 wt % of the negative active material, about 1 wt % to about 5 wt % of the binder, and about 1 wt % to about 5 wt % of the conductive material.

The binder may improve the binding of particles of the negative active material with one another and with a current collector. The binder may include a non-water-soluble binder, a water-soluble binder, or a combination thereof.

The non-water-soluble binder may be selected from polyvinylchloride, carboxylated polyvinylchloride, polyvinylfluoride, an ethylene oxide-containing polymer, polyvinylpyrrolidone, polyurethane, polytetrafluoroethylene, polyvinylidene fluoride, polyethylene, polypropylene, polyamideimide, polyimide, and combinations thereof.

The water-soluble binder may be a styrene-butadiene rubber, an acrylated styrene-butadiene rubber, polyvinyl alcohol, sodium polyacrylate, a copolymer of propylene and a $C_2$ to $C_8$ olefin, a copolymer of (meth)acrylic acid and (meth)acrylic acid alkyl ester, or a combination thereof.

When the water-soluble binder is used as a negative electrode binder, a cellulose-based compound may be further used to increase viscosity as a thickener. The cellulose-based compound may include one or more selected from carboxymethyl cellulose, hydroxypropylmethyl cellulose, methyl cellulose, and alkali metal salts thereof. The alkali metal may be Na, K, or Li. The thickener may be included in an amount of about 0.1 parts by weight to about 3 parts by weight based on 100 parts by weight of the negative active material.

The conductive material may be included to provide or increase electrode conductivity. Any electrically conductive material may be used as a conductive material unless it causes an unwanted chemical change (e.g., chemical reaction). Non-limiting examples of the conductive material include a carbon-based material (such as natural graphite, artificial graphite, carbon black, acetylene black, Ketjenblack, Denka Black, a carbon fiber, and the like); a metal-based material (such as a metal powder and/or a metal fiber including copper, nickel, aluminum silver, and the like); a conductive polymer (such as a polyphenylene derivative); and mixtures thereof.

The current collector may include one selected from a copper foil, a nickel foil, a stainless steel foil, a titanium foil, a nickel foam, a copper foam, a polymer substrate coated with a conductive metal, and combinations thereof.

The positive active material layer and the negative active material layer may each be formed by mixing an active material, a binder, and optionally a conductive material in a solvent to prepare an active material composition, and coating the active material composition on a current collector. The details and parameters of this electrode formation method may be similar to those used in the related art. The solvent may include N-methylpyrrolidone and the like, but embodiments of the present disclosure are not limited thereto. When a water-soluble binder is used in the negative active material layer, the solvent used for preparing the negative active material composition may be or include water.

In some embodiments, a separator may be positioned between the positive electrode and the negative electrode, depending on the format of the rechargeable lithium battery. The separator may include polyethylene, polypropylene, polyvinylidene fluoride, and multiple layer structures thereof (such as a polyethylene/polypropylene double-layered separator, a polyethylene/polypropylene/polyethylene triple-layered separator, or a polypropylene/polyethylene/polypropylene triple-layered separator).

FIG. 1 is an exploded perspective view of a rechargeable lithium battery according to an embodiment of the present disclosure. The rechargeable lithium battery according to an embodiment of the present disclosure is illustrated as a pouch-type (e.g., pouch format) battery, but embodiments of the present disclosure are not limited thereto, and may include various other battery shapes and formats (such as a cylindrical battery, a prismatic battery, and the like).

Referring to FIG. 1, a rechargeable lithium battery 100 according to an embodiment of the present disclosure includes an electrode assembly 110 (manufactured by winding a separator 30 between a positive electrode 10 and a negative electrode 20), a case 120 including the electrode assembly 110, and an electrode tab 130 that provides an electrical path to externally draw currents generated in the electrode assembly 110. The case 120 is sealed by overlapping the two sides facing each other. An electrolyte solution is injected into the case 120 including the electrode assembly 110, such that the positive electrode 10, the negative electrode 20, and the separator 30 are impregnated in the electrolyte solution.

Hereinafter, examples of the present disclosure and comparative examples are described. These examples, however, are not to be interpreted as limiting the scope of the disclosure.

Example 1

An electrolyte for a rechargeable lithium battery was prepared by adding 1.15 M LiPF$_6$ to a mixed solvent of ethylene carbonate and ethylmethyl carbonate (at a volume ratio of 3:7), and then adding 0.5 wt % of an additive represented by Chemical Formula 1a, 5 wt % of fluoroethylene carbonate, and 1 wt % of vinylene carbonate to 100 wt % of the mixture.

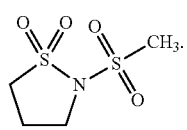

Chemical Formula 1a

Example 2

An electrolyte for a rechargeable lithium battery was prepared according to substantially the same method as Example 1, except that the amount of the additive represented by Chemical Formula 1a was changed to 1 wt %.

Example 3

An electrolyte for a rechargeable lithium battery was prepared according to substantially the same method as Example 1, except that the amount of the additive represented by Chemical Formula 1a was changed to 2 wt %.

Comparative Example 1

An electrolyte for a rechargeable lithium battery was prepared by adding 1.15 M LiPF$_6$ to a mixed solvent of ethylene carbonate and ethylmethyl carbonate (at a volume ratio of 3:7), and then adding 5 wt % of fluoroethylene carbonate, 1 wt % of vinylene carbonate, and 2 wt % of propane sultone to 100 wt % of the mixture.

Comparative Example 2

An electrolyte for a rechargeable lithium battery was prepared by adding 1.15 M LiPF$_6$ to a mixed solvent of ethylene carbonate and ethylmethyl carbonate (at a volume ratio of 3:7), and then adding 1 wt % of an additive represented by Chemical Formula 4, 5 wt % of fluoroethylene carbonate, and 1 wt % of vinylene carbonate to 100 wt % of the mixture.

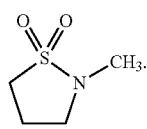

Chemical Formula 4

\* Evaluation of Cyclic Voltammetry (CV) Characteristics

Figure 2:
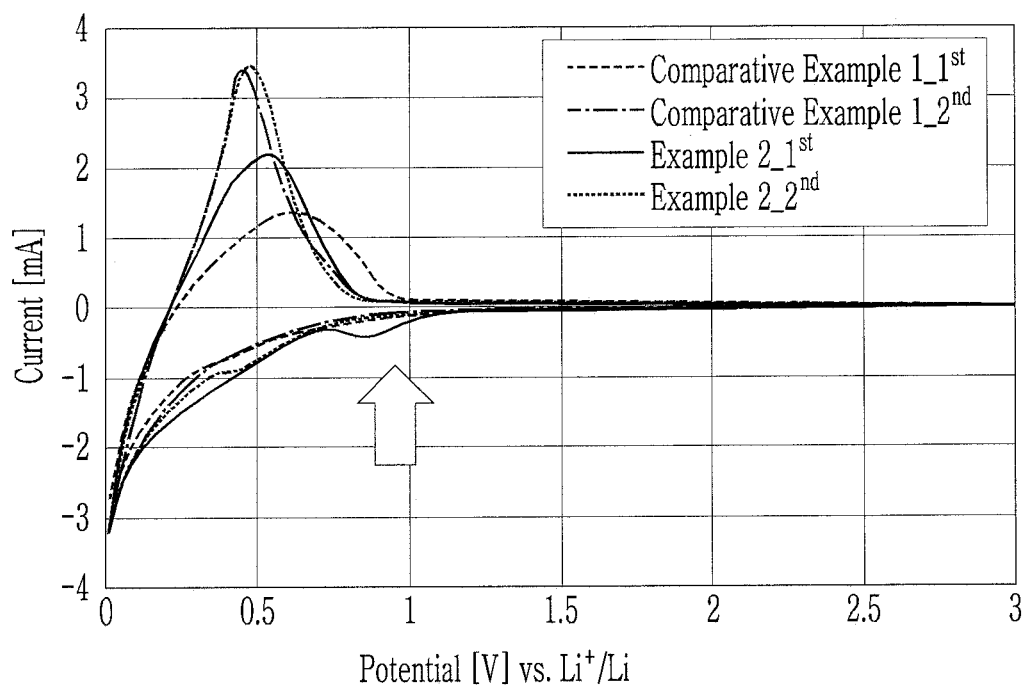
FIG. 2 is a plot showing cyclic voltammogram (CV) results of the electrolytes according to Example 2 and Comparative Example 1.

A cyclic voltammogram (CV, scan rate: 0.1 mV/sec; number of scan cycle: two (2) cycles; graphite working electrode; lithium (Li) metal counter electrode; lithium (Li) metal reference electrode) with three electrodes was measured of the electrolyte according to Comparative Example 1, and the result is shown in FIG. 2. In addition, a CV (scan rate: 0.1 mV/sec; graphite working electrode; lithium (Li) metal counter electrode; lithium (Li) metal reference electrode) with three electrodes was measured of the electrolyte of Example 2, and the result is also shown in FIG. 2.

As shown in FIG. 2, the electrolyte of Example 2 showed a reaction (e.g., an oxidation current peak) during the first cycle (Example 2_1st) at a lower potential than Comparative Example 1, and thus showed increased reactivity at the negative electrode. In addition, the electrolyte of Example 2 showed a first cycle decomposition (reduction) peak around about 0.8 V (arrow), while the electrolyte of Comparative Example 1 showed no analogous decomposition peak. The electrolyte of Example 2 showed a reaction at a higher (more positive) potential than ethylene carbonate (which would appear as a reduction peak at 0.5 V), suggesting that one or more components of the electrolyte in Example 2, such as the additive, is reduced earlier than ethylene carbonate. When an electrolyte (e.g., one or more components in the electrolyte, such as an additive) is reduced earlier than ethylene carbonate, the electrolyte (component or additive) forms a film on the surface of the negative electrode, and may thereby suppress or reduce an additional decomposition of the ethylene carbonate.

Accordingly, a problem of hindered lithium ion movement (e.g., decreased lithium ion diffusion and/or transport) due to ethylene carbonate decomposition, resulting in solvent depletion of the electrolyte, formation of an EC-derived resistive film, and deteriorated cycle-life characteristics and output characteristics may be prevented or reduced.

Referring to the results, the rechargeable lithium battery cell using the electrolyte of Example 2 formed a film on the negative electrode during the 1$^{st}$ initial charge and discharge, and in addition, this film had small (low) resistance during lithium intercalation/deintercalation.

\* Manufacture of Battery Cell

A positive active material slurry was prepared by mixing 96 wt % of a LiCoO$_2$ positive active material, 2 wt % of a Ketjen black conductive material, and 2 wt % of polyvinylidene fluoride in N-methylpyrrolidone as a solvent. The positive active material slurry was coated on an aluminum foil, and then dried and compressed to manufacture a positive electrode.

A negative active material slurry was prepared by mixing 96 wt % of an artificial graphite negative active material, 2 wt % of a Ketjen black conductive material, and 2 wt % of polyvinylidene fluoride in N-methylpyrrolidone as a solvent. The negative active material slurry was coated on a copper foil, and then dried and compressed to manufacture a negative electrode.

The positive electrode, the negative electrode, and each electrolyte according to Examples 1 to 3 and Comparative Examples 1 and 2 were used to manufacture rechargeable lithium battery cells using the above method. In each cell, the electrolyte solution was injected in an amount of 5.8 g.

\* Thickness Increase Rate of Battery Cell at 85° C.

The rechargeable lithium battery cells using the electrolytes according to Examples 1 to 3 and Comparative Examples 1 and 2 were charged up to 4.4 V at 0.7 C up to 100% SOC (State of Charge) (e.g., a state of full charge, or 100% of charge capacity of the battery cell during the charge/discharge between 2.75 V to 4.4 V), and then stored at 85° C. for 8 hours. The thickness of each battery was measured before and after storage, and the results are shown in Table 1. The results were used to calculate battery thickness increase rates that are also shown in Table 1.

\* Capacity Retention and Recovery Rate at 85° C.

Each rechargeable lithium battery cell using the electrolytes according to Examples 1 to 3 and Comparative Examples 1 and 2 were charged up to 4.4 V at 0.7 C up to 100% SOC (State of Charge) (e.g., a state of full charge, or 100% of charge capacity of the battery cell during the charge/discharge between 2.75 V to 4.4 V), stored at 85° C. for 8 hours, and discharged at 0.2 C to a cut-off voltage of 2.75 V, after which a discharge capacity ratio (e.g., of discharge capacity after high temperature storage relative to at the 1$^{st}$ discharge capacity) was calculated. The results are shown in Table 1.

Subsequently, the rechargeable lithium battery cells were once charged and discharged under the same conditions as above to measure the discharge capacity, and a ratio of the discharge capacity relative to the initial capacity before storage was calculated. The results are shown as a capacity recovery rate in Table 1.

TABLE 1

|  | Thickness before storage (mm) | Thickness after storage (mm) | Thickness increase rate (%) | Capacity retention (%) | Capacity recovery rate (%) |
| --- | --- | --- | --- | --- | --- |
| Comparative Example 1 | 5.145 | 5.458 | 6.09 | 93.5 | 97.0 |
| Comparative Example 2 | 5.145 | 5.568 | 8.23 | 92.0 | 97.0 |
| Example 1 | 5.140 | 5.350 | 4.10 | 93.6 | 98.2 |
| Example 2 | 5.143 | 5.205 | 1.21 | 94.0 | 98.8 |
| Example 3 | 5.140 | 5.213 | 1.42 | 93.8 | 98.9 |

As shown in Table 1, the battery cells using electrolytes including an additive represented by Chemical Formula 1a (Examples 1 to 3) showed a very low thickness increase rate at a high temperature of 85° C. and excellent results in terms of capacity retention and capacity recovery rate, compared with the battery cells using electrolytes including propane sultone (Comparative Example 1) or an additive represented by Chemical Formula 4 (Comparative Example 2).

The battery cells using electrolytes including 1 wt % to 2 wt % of an additive represented by Chemical Formula 1a (Examples 2 and 3) showed very excellent swelling properties and capacity characteristics.

* Thickness Increase Rate of Battery at 60° C.

The rechargeable lithium battery cells using the electrolytes according to Examples 1 to 3 and Comparative Examples 1 and 2 were each charged up to 4.4 V at 0.7 C up to 100% SOC (State of Charge) (e.g., a state of full charge, or 100% of charge capacity of the battery cell during the charge/discharge between 2.75 V to 4.4 V), and then stored at 60° C. for 21 days. The thickness of each battery before and after the storage was measured, and the results are shown in Table 2. The results were used to calculate a battery thickness increase rate, and the results are shown in Table 2.

* Capacity Retention and Recovery Rate at 60° C.

The rechargeable lithium battery cells using the electrolytes according to Examples 1 to 3 and Comparative Examples 1 and 2 were charged up to 4.4 V at 0.7 C up to 100% SOC (State of Charge) (e.g., a state of full charge, or 100% of charge capacity of the battery cell during the charge/discharge between 2.75 V to 4.4 V), stored at 60° C. for 21 days, and then discharged at 0.2 C to a cut-off voltage of 2.75 V. A ratio of the discharge capacity after storage relative to the 1$^{st}$ discharge capacity was calculated, and the results are shown in Table 2.

Subsequently, the rechargeable lithium battery cells were once charged and discharged under the same conditions as above to measure discharge capacity, and a ratio of the discharge capacity relative to the initial capacity before storage was calculated. This ratio is shown as a capacity recovery rate in Table 2.

TABLE 2

|  | Thickness before storage (mm) | Thickness after storage (mm) | Thickness increase rate (%) | Capacity retention (%) | Capacity recovery rate (%) |
| --- | --- | --- | --- | --- | --- |
| Comparative Example 1 | 5.140 | 5.521 | 7.41 | 86.3 | 97.0 |
| Comparative Example 2 | 5.140 | 6.270 | 22.01 | 87.0 | 96.9 |
| Example 1 | 5.141 | 5.360 | 4.26 | 87.0 | 97.2 |
| Example 2 | 5.139 | 5.230 | 1.77 | 88.0 | 97.6 |
| Example 3 | 5.140 | 5.240 | 1.95 | 88.0 | 97.5 |

As shown in Table 2, the battery cells using the electrolytes including an additive represented by Chemical Formula 1a (Examples 1 to 3) showed a very small thickness increase rate and excellent results in terms of capacity retention and capacity recovery rate, despite long-term storage at a high temperature of 60° C., compared with the battery cells using electrolytes including propane sultone (Comparative Example 1) or an additive represented by Chemical Formula 4 (Comparative Example 2).

The battery cells using the electrolyte including 1 to 2 wt % of an additive represented by Chemical Formula 1a (Examples 2 and 3) showed excellent swelling properties and capacity characteristics.

As used herein, the terms "use", "using", and "used" may be considered synonymous with the terms "utilize", "utilizing", and "utilized", respectively. Further, the use of "may" when describing embodiments of the present disclosure refers to "one or more embodiments of the present disclosure".

As used herein, the terms "substantially", "about", and similar terms are used as terms of approximation and not as terms of degree, and are intended to account for the inherent deviations in measured or calculated values that would be recognized by those of ordinary skill in the art.

Also, any numerical range recited herein is intended to include all sub-ranges of the same numerical precision subsumed within the recited range. For example, a range of "1.0 to 10.0" is intended to include all subranges between (and including) the recited minimum value of 1.0 and the recited maximum value of 10.0, that is, having a minimum value equal to or greater than 1.0 and a maximum value equal to or less than 10.0, such as, for example, 2.4 to 7.6. Any maximum numerical limitation recited herein is intended to include all lower numerical limitations subsumed therein and any minimum numerical limitation recited in this specification is intended to include all higher numerical limitations subsumed therein. Accordingly, Applicant reserves the right to amend this specification, including the claims, to expressly recite any sub-range subsumed within the ranges expressly recited herein.

While this disclosure has been described in connection with what is presently considered to be practical example embodiments, it is to be understood that the disclosure is not limited to the disclosed embodiments. On the contrary, it is intended to cover various modifications and equivalent arrangements included within the spirit and scope of the appended claims and equivalents thereof. Therefore, the aforementioned embodiments should be understood to be exemplary but not limiting the present disclosure.

What is claimed is:

1. An electrolyte for a rechargeable lithium battery, comprising:
   a non-aqueous organic solvent;
   a lithium salt; and
   an additive represented by Chemical Formula 1:

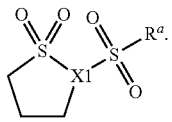

Chemical Formula 1 wherein in Chemical Formula 1,
X1 is CH or a nitrogen atom (N), and $R^a$ is a substituted or unsubstituted alkyl group.

2. The electrolyte for a rechargeable lithium battery of claim 1, wherein an amount of the additive is about 0.1 wt % to about 3 wt % based on a total weight of the electrolyte.

3. The electrolyte for a rechargeable lithium battery of claim 1, wherein an amount of the additive is about 1 wt % to about 2 wt % based on the total weight of the electrolyte.

4. The electrolyte for a rechargeable lithium battery of claim 1, wherein the substituted alkyl group is a fluorine-substituted alkyl group.

5. The electrolyte for a rechargeable lithium battery of claim 1, wherein the electrolyte further comprises a second additive selected from fluoroethylene carbonate, vinylene carbonate, succinonitrile, hexane tricyanide, $LiBF_4$, and combinations thereof.

6. The electrolyte for a rechargeable lithium battery of claim 5, wherein an amount of the second additive is about 5 wt % to about 20 wt % based on a total weight of the electrolyte.

7. The electrolyte for a rechargeable lithium battery of claim 1, wherein X1 is CH.

8. The electrolyte for a rechargeable lithium battery of claim 1, wherein X1 is N.

9. The electrolyte for a rechargeable lithium battery of claim 1, wherein Ra is a substituted or unsubstituted methyl group, a substituted or unsubstituted ethyl group, a substituted or unsubstituted propyl group, a substituted or unsubstituted butyl group, a substituted or unsubstituted pentyl group, and a substituted or unsubstituted hexyl group, a substituted or unsubstituted heptyl group, a substituted or unsubstituted octyl group, a substituted or unsubstituted nonyl group, a substituted or unsubstituted decyl group, a substituted or unsubstituted dodecyl group, a substituted or unsubstituted isopropyl group, a substituted or unsubstituted sec-butyl group, a substituted or unsubstituted isobutyl group, a substituted or unsubstituted neopentyl group, or a substituted or unsubstituted isopentyl group.

10. The electrolyte for a rechargeable lithium battery of claim 1, wherein the additive is further represented by Chemical Formula 1a:

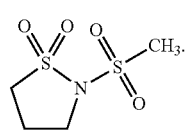

Chemical Formula 1a

11. The electrolyte for a rechargeable lithium battery of claim 1, wherein the additive is further represented by Chemical Formula 1b:

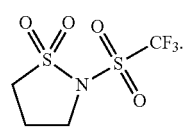

Chemical Formula 1b

12. A rechargeable lithium battery comprising:
    a negative electrode comprising a negative active material layer comprising a negative active material;
    a positive electrode including a positive active material layer comprising a positive active material; and
    the electrolyte of claim 1.

13. The rechargeable lithium battery of claim 12, wherein the negative electrode further comprises a stable passivation film on the surface of the negative active material layer in contact with the electrolyte, the stable passivation film comprising a reduction-decomposition product of the additive.

* * * * *